(12) United States Patent
Giannadakis

(10) Patent No.: US 6,706,050 B1
(45) Date of Patent: Mar. 16, 2004

(54) SYSTEM OF LAPAROSCOPIC-ENDOSCOPIC SURGERY

(76) Inventor: Emmanuil Giannadakis, 4-6 Makrinitsis St., Athens 115 22 (GR)

( * ) Notice: Subject to any disclaimer, the term of this patent is extended or adjusted under 35 U.S.C. 154(b) by 0 days.

(21) Appl. No.: 08/983,351
(22) PCT Filed: May 10, 1996
(86) PCT No.: PCT/GR96/00012
§ 371 (c)(1),
(2), (4) Date: Feb. 3, 2000
(87) PCT Pub. No.: WO97/42889
PCT Pub. Date: Nov. 20, 1997
(51) Int. Cl.[7] ............................................... A61B 17/34
(52) U.S. Cl. ...................................... 606/185; 604/164
(58) Field of Search ................................ 606/185, 170, 606/210; 604/164, 264

(56) References Cited

U.S. PATENT DOCUMENTS 3,789,852 A   2/1974   Kim et al. ................... 128/347
5,620,456 A * 4/1997   Sauer et al. ................. 606/185
6,454,783 B1 * 9/2002   Piskun ........................ 606/185

FOREIGN PATENT DOCUMENTS

EP   0646358   4/1995
WO   9300946   1/1993

* cited by examiner

Primary Examiner—Kevin T. Truong
(74) Attorney, Agent, or Firm—Ladas & Parry

(57) ABSTRACT

An apparatus for laparoscopic-endoscopic surgery is arranged to accommodate a plurality of different surgical instruments and to penetrate the abdominal wall through a single hole. The apparatus includes a piercing laparoscopic cylinder (1), equipped at its external orifice with a multi-instrument base (11, 12, 13) provided with a plurality of holes (14, 15) for receiving said surgical instruments. The piercing laparoscopic cylinder is transversely extendible, the multi-instrument base (12, 12, 13) is elongate and comprises longitudinal ducts registering with holes (14, 15). The apparatus also has a reducer (2) capable of introduction into the piercing laparoscopic cylinder and a number of dividers (3) of variable form and size adapted to be detachably introduced and fitted into the reducer.

16 Claims, 6 Drawing Sheets

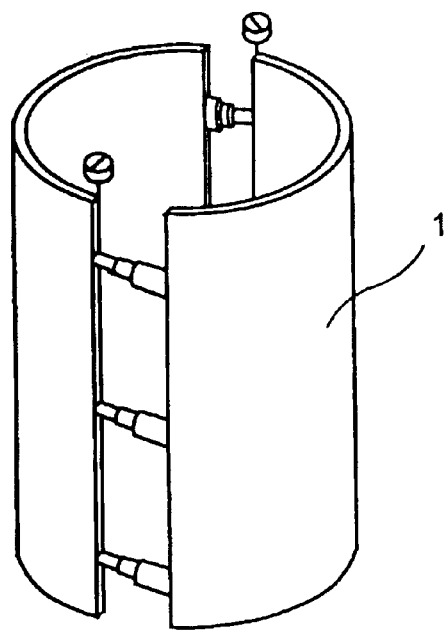
F I G. 1
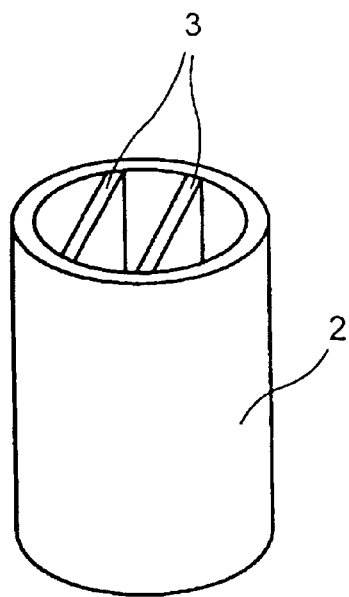
F I G. 2

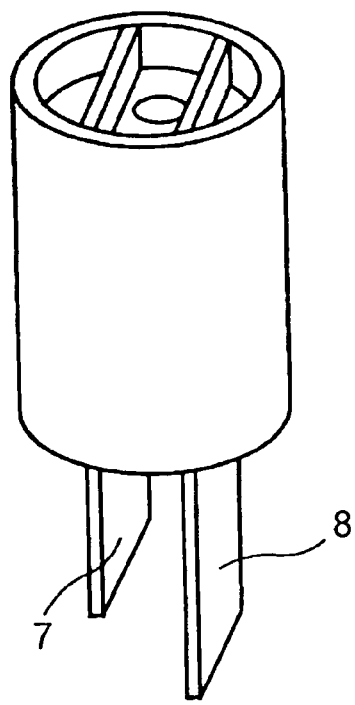
F I G. 5
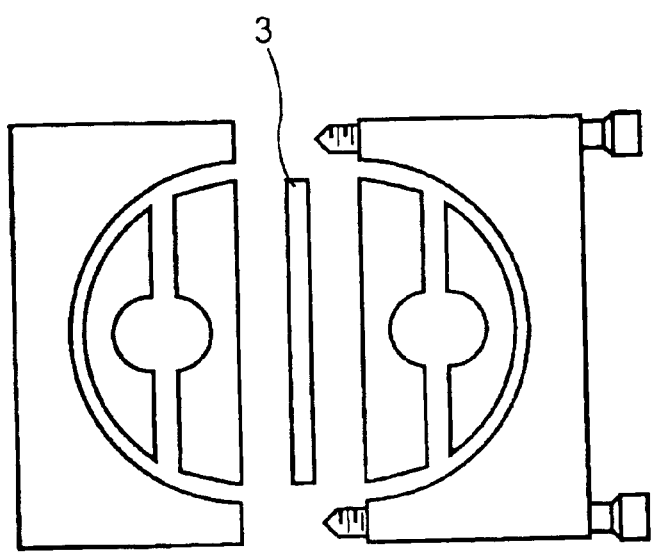
F I G. 6

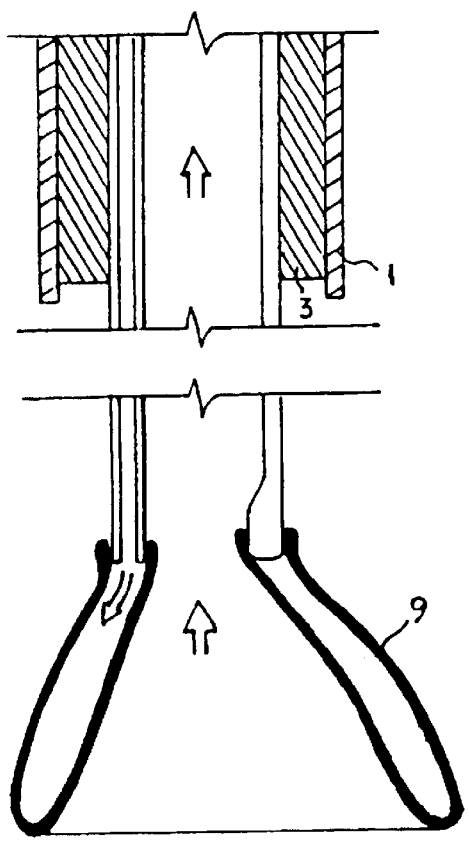
FIG. 7A
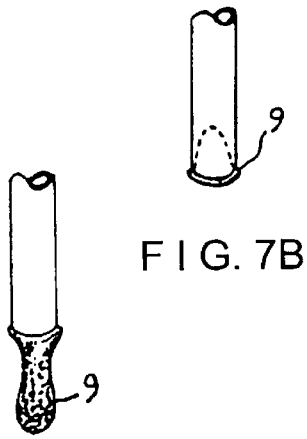
FIG. 7B
FIG. 7C
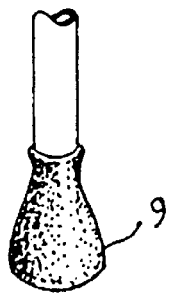
FIG. 7D
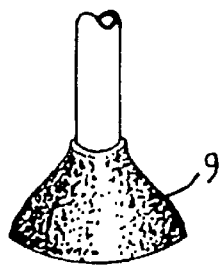
FIG. 7E

SYSTEM OF LAPAROSCOPIC-ENDOSCOPIC SURGERY

The invention pertains to a laparoscopic surgical system designed to make possible the entry of various laparoscopic instruments into the human body. The present system provides the possibility of simultaneous use of more than one instruments from one and only one hole of the wall over the (intervent) area under surgery, and also of modified currently available laparoscopic-endoscopic instruments as well as the introduction of other surgical instruments.

The entry of laparoscopic instruments into the human body has until now been obtained by means of the insertion through a single aperture of a special type piercing laparoscopic cylinder or port ("TROCAR") which may be equipped with reducers. The currently existing laparoscopic TROCARS with a single hole have certain disadvantages in spite of their wide use. For example, they afford a limited space for easy manipulation, necessitate larger and numerous incisions and consequently a larger numbers of scars as well as miore time, preclude the use of curved instruments as well as increase the possibility of leakage of inflatory gas and therefore overburden the entire surgical operation. Further more the existing laparoscopic instruments hinder the easy and effective grasping of viscera.

The present invention is designed to introduce a laparoscopic surgical system capable of making a larger number of manipulations and of facilitating the use of various instruments, the ultimate result being the reduction of operation time, anesthesia time (thus reducing cost) an improved post operational condition for the patient (less morbidity and hospital time) and better aesthetic result.

The present system can achieve the introduction of numerous laparoscopic instruments by means of a mechanically extendible laparoscopic cylinder through a single hole through the abdominal wall rather than through numerous holes as was the practice until now. The entire process involved by this method is mechanically achieved by means of a diaphragm having numerous patterns and sizes thus affording a high degree of interchangeability.

The main advantages of the proposed system are the following:

1. More space through a single hole and capability of using a multiport system with or without a diaphragm as well as the use of a simple reducer.
2. External and internal minimization of traumatic area (less scars, better aesthetic result).
3. Compatibility and more effective combination of proposed system with open surgery instruments.
4. Accommodation of instruments of various sizes.
5. Easy handling of multiport system and diaphragm by the TROCAR.
6. Performance of laparoscopic operations which have been impossible or extremely difficult up to now.
7. Optimization of the most functional internal space of TROCAR.
8. Simultaneous introduction of more than one instruments.
9. Single hand manipulation by the surgeon working through a single orifice on the human body.
10. Considerable saving of time and minimum number of manipulations.
11. Possibility of introducing a proposed bent camera and proposed bent instruments of this system or future curved instruments.
12. Reduction of anesthesia time.
13. During the surgical or laparoscopic operation it is possible by means of the laparoscopic sucker to grasp the slippery viscera, which cannot be easily held by ordinary surgical instruments, and it permits movements of them (viscera) with less lesions because of broad adhering surface that minimizes local pressures.
14. More effective and multi-operational combination of open surgery with the proposed system.
15. Higher operational efficiency by combining either endoscopic, diagnostic or therapeutic procedures (ultrasonic heads, endoscopic camera or various endoscopic catheters and instruments with proposed system). This is achieved by employing:
    a. the multiport system and
    b. by means of a sucker which allows the insertion of other smaller laparoscopic instruments through its hole for the operation on concave viscera.
16. The control of quick stop of intraperitoneal hemorrage from all peritoneal concave and solid organs.
17. The closure of iatrogenic or traumatic appertures as well as the stopping of leakage of fluid from internal concave organs achieved by the sucker (less morbidity-infections, less complications and less re-operations).

A description of the invention follows with the aid of examples and references to the attached drawing, wherein:

FIG. 1 is a top/left-side/front perspective view of an extendible piercing laparoscopic cylinder (TROCAR);

FIG. 2 is a top/left-side front perspective view of a reducer and diaphragms therefor;

FIG. 5 is a top/left-side/front perspective view of a reducer and shallow and deep diaphragms therefor;

FIG. 6 is a top plan view of another, fragmented-based embodiment of the cylinder of FIG. 1;

FIG. 7A is a front elevational view, partly cut away and partly in section of a lararoscopic sucker, together with FIGS. 7B to 7E (collectively referred to below as FIG. 7), which are top/front perspective views thereof;

FIG. 1 illustrates a side view of the extendible piercing laparoscopic cylinder 1 (TROCAR) combined with a multiport system of laparoscopic instruments. This cylinder can be introduced into an orifice of the abdominal area. Through this TROCAR the surgeon can introduce more than one laparoscopic instruments with the additional advantage of doing it simultaneously. This can be achieved through the longitudinal separation of the TROCAR with the aid of one or more diaphragms 3. This particular TROCAR is divided into two or more parts and this arrangement enables it to adapt its size to the operational requirements A reducer (divertor) of appropriate diameter is introduced lengthwise into the TROCAR and is designed to ensure the airtightness and antibacterial protection of the abdominal area. A thin expandable film is placed on the top part of the TROCAR to seal the system's airtightness, after having removed the piercing shaft.

This TROCAR system, if combined with the well-known self-extended abdominal orifice, may achieve the minimization of traumatic area through the optimum use of a single hole. This arrangement results in permitting the surgeon to perform easy manipulations within the minimum time and to reduce all traumatic adverse effects.

One or more diaphragms 3 can be introduced and fitted into the reducer 2 lengthwise, as illustrated in FIG. 2. Also the reducer cylinder (divertor) may by construction have appropriately fitted detachable diaphragms.

This inserted cylindrical reducer may be extended at will beyond the bottom part of the TROCAR within the abdominal area, namely at the contact point of the organs to be operated on in such a way as to make possible the easy use of certain apparatus such as a special type camera, when it is necessary to intervene in special type of endoscopic operations.

Figure 3:
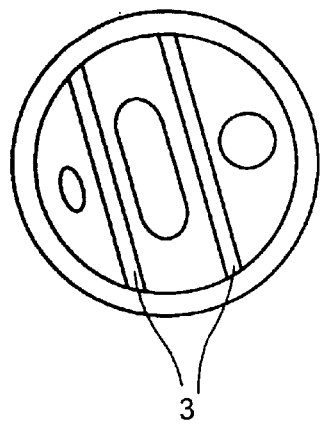
FIG. 3 is a top plan view of the reducer and diaphragms.

FIG. 3 indicates a top view of a multiport diaphragm, which has a variable distance between the hole centers, a different pattern of holes and a variable depth in such a way as to have the possibility of interchangeability as regards its detachable diaphragms 3. This arrangement or layout, which may be adjusted depending on the surgeon's requirements, can insure through the use of a given diameter reducer the introduction of laparoscopic instruments of varying sizes as well as the introduction of varying sizes instruments used in open surgery such as various types of staplers.

Figure 4A:
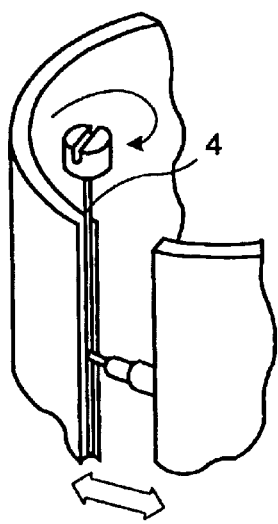
FIGS. 4A and 4B are enlarged left-side perspective views of portions of the cylinder of FIG. 1.
Figure 4B:
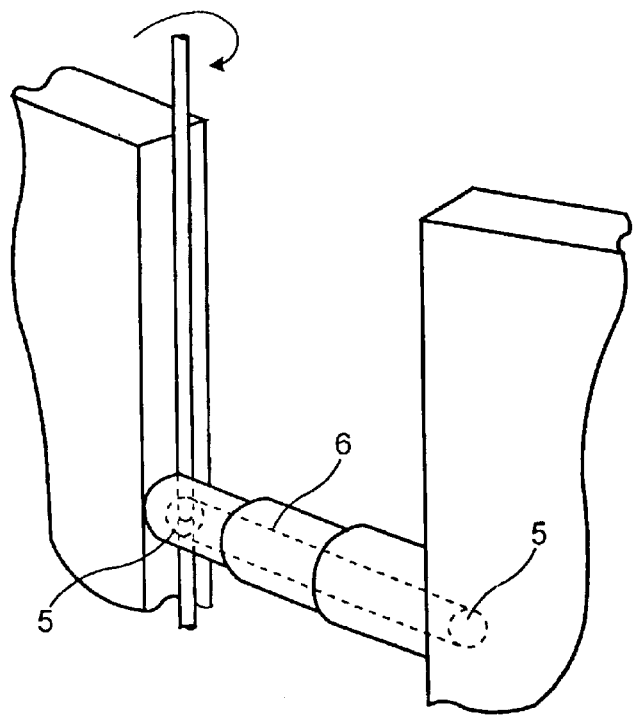

FIG. 4A and FIG. 4B show in detail the expansion and contraction mechanism of the proposed TROCAR. A shaft 4 running parallel to the longitudinal axis of the TROCAR located on one edge of the cylindrical surface bears a metal gear 5 around which a metal fiber 6 is wound. This fiber is connected to another gear which is fixed on the opposite edge of the longitudinally divided TROCAR. When the metal shaft turns clockwise, the TROCAR expands, while when it turns anti-clockwise, the TROCAR contracts in such a way as to accommodate variable size reducers at will.

FIG. 5 illustrates a shallow 7 and a deep 8 diaphragm. The shallow diaphragm insures a high degree of mobility and cross handling of the instruments. The deep diaphragm acts as a viscera pushing device in the proximity of the organ being operated on, provided that the remaining holes are eliminated except for the operationally active.

Another possibility of the proposed invention, namely the fragmented base, is illustrated in FIG. 6. This fragmented base is suitable for the introduction of large size instruments. It may be disassembled at will to accommodate such large size instruments and immediately afterwards can be assembled once again around their shafts, that are smaller in diameter than their apex or their handles, leaving their handles outside the organ area operated on within easy reach.

FIG. 7 indicates a laparoscopic sucker 9, which is a part of the present invention and is designed to grasp and adhere on to the viscera not easily held by conventional instruments of present technology such as forceps etc. A hemispherical contact area is formed through an adjustable air-flow under pressure fed through the sucker's concave shaft. This surface having an appropriate curvature can grasp, lift, be fitted or adhered on to the viscera being operated on.

In order that the sucker may have the desired rigidity and may pass through the hole of the extendible cylinder, while retaining a satisfactory degree of flexibility necessary for acquiring an optimum curvature and for obtaining the maximum grasping of viscera, it is made of elastic material, such as transparent rubber necessary to watch the internal manipulations, or of thin metallic foil of a predetermined extendible form and size. The sucker's shape is obtained by feeding gas under pressure and can vary its functional size from a minimum to a maximum. The gas flow passes through a side hole on the sucker's metal shaft while positive pressure is retained through the use of a one way valve located within the sucker gas feeding line. At the level of the handle of the sucker instrument, which makes an angle with the longitudinal axis of the sucker shaft, there is a port supplying negative pressure (suction). At the handle of the sucker there is another port, equipped with a one way valve, which permits the entrance of minature endoscopic instruments, catheters, cameras etc, for the interior surgery of internal organs. The afforementioned instruments pass through the entire length of the sucker shaft as well as the sucker cavity and into the adhered organ being operated on.

Figure 8A:
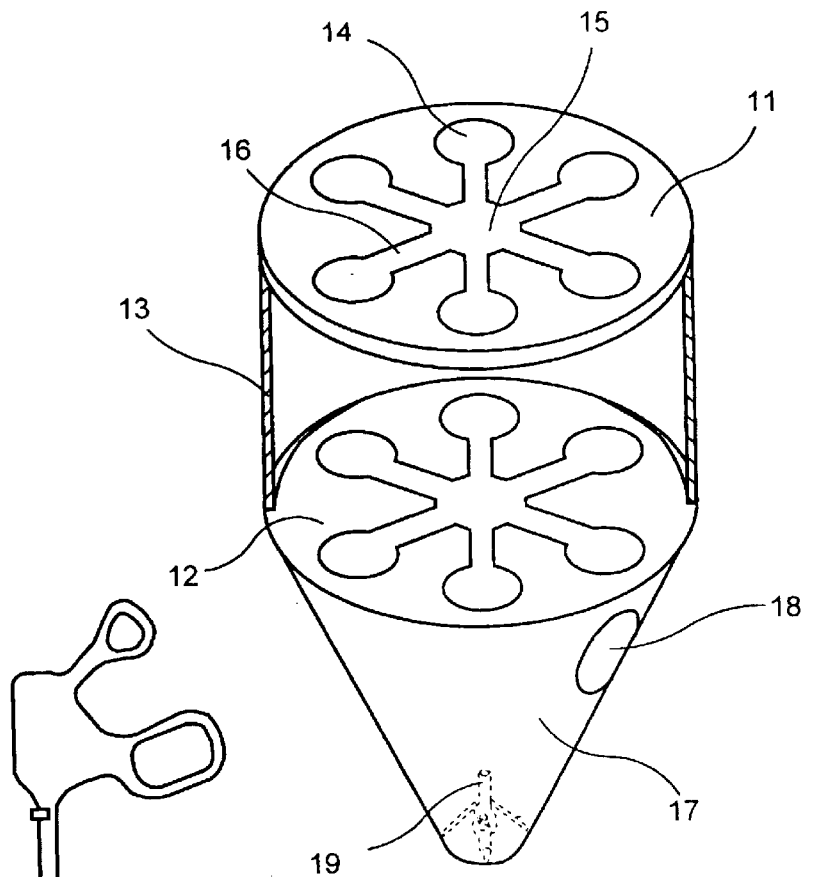
FIGS. 8A and 8C are enlarged top/front perspective views of portions of a multi-instrument shown in the top/front perspective view of FIG. 8B.
Figure 8B:
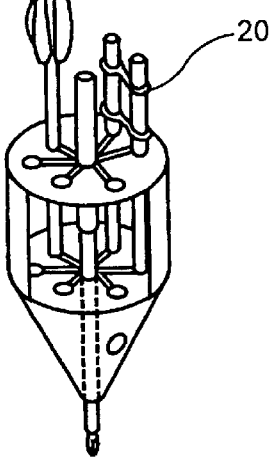
Figure 8C:
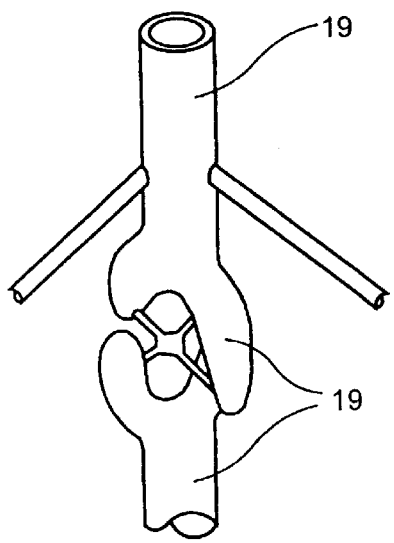

The multi-instrument resembles a revolver mill, see FIG. 8. It consists of a top 11 and a bottom 12 circular metal plate interconnected with another via a cylindrical metal surface 13. Both circular plates have a number of circumferential holes 14 as well as a central hole 15 in such a way that each one of the top holes is perfectly aligned with its corresponding bottom hole. Thus, if the top surface is a seven-port plate (six circumferential and one central) then the bottom surface is also a seven port plate with its holes exactly underneath the top surface. In this example, therefore, seven vertical ducts are formed capable of accommodating six (one has to remain empty for motion freedom) different laparoscopic or endoscopic instruments. Furthermore, each one of the circumferential ducts is connected with the central one through a radial slot 16. The width of each slot is such so as to permit the easy sliding of a laparoscopic or an endoscopic instrument from a given circumferential duct of the multi-instrument's to its central duct and vice versa.

With the exception of the central duct and one circumferential duct, all other ones are blind holes, i.e., they are used to accommodate laparoscopic or endoscopic instruments as a storage chamber. The central duct runs along the entire multi-instrument and is used to accommodate the laparoscopic instrument performing the operaion at that time. The bottom plate is connected to a conical surface. Specifically it is an inverted frustrum of a cone 17, the large base of which has the same diameter as the bottom plate and the small base of which has an inner diameter (ID) equal to that of the central port's diameter. The outer diameter (OD) of the small base is a little larger than the ID depending on the metal thickness which the metal multi-instrument is made of. The aforementioned circumferential duct terminates at the conical surface and is a permanently open hole 18, equipped with a one way valve to preclude gas leakage for the utilization of an extra forceps.

Typically, the dimensions in (mm) of such a multi-instrument are as follows:

CYLINDER HEIGHT=90, CYL. DIAMETER=50 OD, CONE HEIGHT=60 DUCT DIAMETER=8, SLOT LENGTH=2, SLOT WIDTH 7.

FIG. 8 is a detail of a universal joint 19 used to achieve at least two degrees of freedom for the laparoscopic instrument performing the operation.

Figure 9:
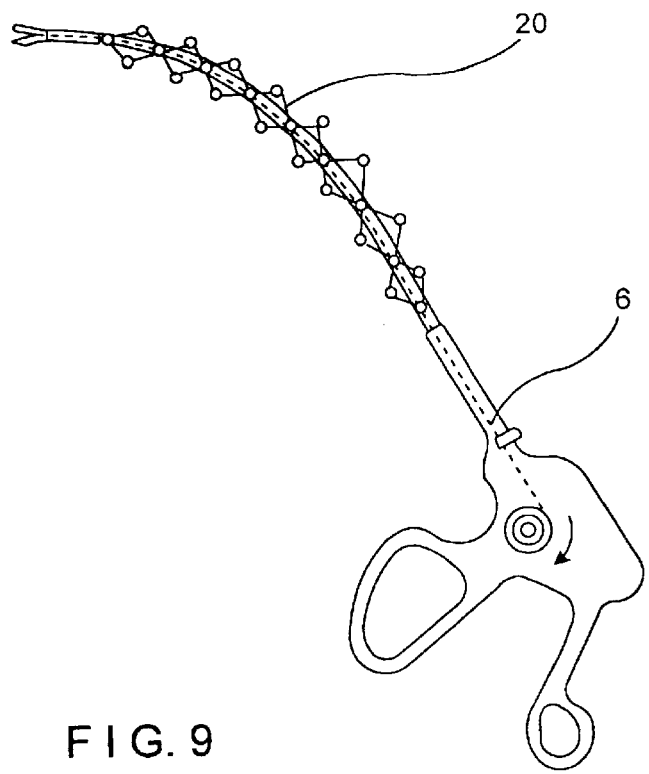
FIG. 9 is a left-side elevational view of a scissors-like system.
Figure 10:
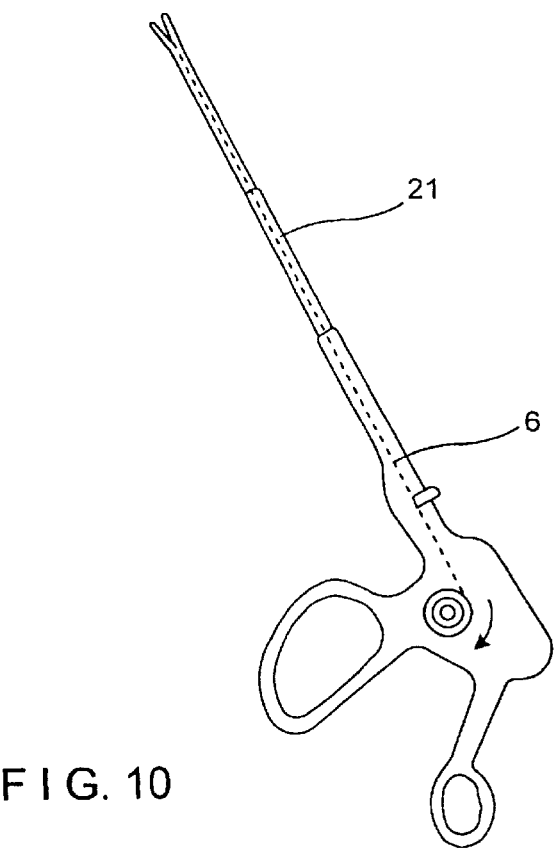
FIG. 10 is a left-side elevational view of a telescopic system.

FIG. 9 and FIG. 10 illustrate the implemetation of a scissors-like 20 and a telescopic 21 systems respectively. Both achieve operations at variable depths with high degree of precision but the former one permits operations at variable agles as well.

Notice that the handles of the proposed modified instruments resemble those of the currently available ones, with the exception that they differ in that they are equipped with a mechanism capable of extending or retracting their length telescopically.

Furthermore, the proposed instruments have similar functions with the others in trade, e.g., rotation, grasping, coagulation, cutting, flexion etc. With respect to the proposed telescopically extendable instruments, their handles are equipped with a spool containing metal wire that can turn clockwise or anti-clockwise (telescopic extension or retraction of the instrument). Depending on the TROCAR length and at a given corresponding point of the instrument's length the wire is unraveled and achieves a maximum predetermined instrument length telescopically, and also may, at the surgeon's will, stop at any intermidiate length determined by a special pin (see FIG. 10) attached on to the center of the handle spool. Also there is a microdiaphragm within the interior of the smallest diameter extreme cylinder. This microdiaphragm is used to separate the two wires from each other, i.e., the one used for operating the motion of the graspers or scissors head and the other one for the extension/retraction of the instrument itself motion. Finally, the space for retraction of the telescopically extendable concentric cylinders lies between the handle and internal orifice of the TROCAR divertor. Instruments commonly known as the laparoscopic hook and the laparoscopic ball need neither a microdiaphragm nor the corresponding wire for the incising or grasping motion With respect to the laparoscopic instruments equipped with a scissors-like extendable mechanism, their handles are constructed similarly (spool, pin, wire) to those of the telescopically extendable instruments. Notice, that when the instrument is at a neutral position, the shaft is completely straight whereas when the handle spool is turned clockwise a desired flexion is attained. This is achieved trough the fact that the scissors arms are of unequal length which provide peferential flexion to one side up to a maximum curving. In addition, their hollow shafts, beyond a certain point of their length, are made of a flexible material which can closely follow the precise angle of flexion determined by the scissors-like mechanism in conjunction with the handle's pin position. Notice that telescopic and the scissors-like systems may be combined in the same instrument, with the following modification their main bodies must be activated by two separate wires while their handles must be equipped with two sets of the spool-pin mechanism, each set of a different color for easy distinction, e.g., red spool for telescopic extension and green spool for scissors curving.

The present system is principally designed to perform laparoscopic and combined endoscopic surgical operations as well as laparoscopic operations involving the use of large size open surgery instruments.

The introduction of the proposed TROCAR system through a single orifice of the abdominal wall makes possible the passage and contact of the abdominal cavity (peritoneal cavity) with the external area through his TROCAR duct-cylinder, which is rigidly attached to the entire thickness of abdominal wall after having pierced it. This hole is opened by means of a simple Veres needle or directly via the piercing stylus of the TROCAR system following a small (5 mm–10 mm) incision on the abdominal wall.

The abdomen is inflated with $CO_2$ or other compatible with laparoscopic surgery gas either by means of a special type Veres needle adapter or by means of a special type air adapter of the TROCAR system. If the piercing stylus (shaft) is directly used, it must be preceded by a small boring of variable size at the surgeon's discretion and depending on the final TROCAR diameter opening, which is made on the abdominal tissue with the use of a small knife.

The abdominal holes (and the corresponding number of TROCARs used) vary according to the type of the surgical operation. It should be noted that a special type self expansible material may be used as an external expandable film on the base of the TROCAR prior to its insertion into the abdomen which is obtained through circular oscillating moves. Once the surgeon inserts the appropriate reducer within the TROCAR, the expandable film, acting as a gas seal, is pierced and pushed onto one side of the reducer's cavity. Therefore, the endoscopic instrument can freely operate via the proposed TROCAR system.

The piercing stylus is removed upon the insertion of the TROCAR into the abdomen thus leaving inside only the cylindrical duct, which is connected to an appropriate rubber hose designed to feed additional gas into the abdomen in case of depletion. The duct is also equipped with a one way valve which prevents the leakage of $CO_2$ gas through the system. This is immediately followed by the TROCAR expansion to the desired diameter by means of rotating screws. In this way the cylinder is extended according to the surgeon's requirements. As soon as the desired diameter is obtained, the protective expandable film is removed from the upper surface of the TROCAR system and the multiport diaphragm system is introduced through the cylinder and the valve. The multiport diaphragm is fixed by means of clips on the external part of the cylinder. It consists of two or more removable or permanently fixed parts interconnected by means of a clip-on arrangement.

If more space is needed, we may use a diaphragm of great depth which can push downwards the patient's adjacent organs.

The diaphragm is either preliminary clipped on or is directly placed into the cylinder. One or more diaphragms may be used depending on the diameter of the cylinder, the requirements of the surgical operation, the usage of surgical operation, the usage of surgical instruments through the diaphragm channels and the surgeon's dexterity. Mechanical fasteners 20 (FIG. 8) such as metal clips used to connect endoscopic, laparoscopic or surgical instruments with one another allow the surgeon considerably greater ease of operation since more than one instruments are manipulated by a single hand simultaneously.

We can introduce various instruments through the holes which exist in the variable diaphragm system and which have different sizes and shapes (round or oval) or which are formed by connecting together the parts of a disassembled base clipped on the main shaft. These instruments may be of the existing laparoscopic type, or they may also be of a larger size of general surgery as well as the proposed bent instruments of telescopic type which afford an increased manipulatory ease due to a greater bending angle.

In case the multi-instrument or a general surgery large size instrument is used, no diaphragm will be used in the system. The proposed instruments of the telescopic system and the scissors system have a shape and function similar to that of the existing instruments (scissors opening or shaft rotation) blit they differ in respect of the angle of bending and of the depth variability according to the surgeon's requirements.

They are interconnected by means of external clips which make possible their simultaneous motion in unison.

The multi-instrument facilitates the surgeon's work, who takes advantage of the elasticity of the abdominal wall because he can use through a single opening 11 various adjacent instruments depending on his needs, which he may shift on to the central hole at a time.

The sucker contains its own suction system of negative pressure and a one way valve. Negative pressure is achieved by connecting the sucker's central shaft with a vacuum pump in series with a sensitive manometer and/or flow meter. This less than atmospheric pressure is retained under the cavity of the sucker by the use of a one way valve of a "butterfly" type of vane. It is possible to introduce through the sucker's hollow shaft 12 other instruments such as "Fogarty", small "Folley", "Nelaton pipes" or other suckers of a smaller size, choledechoscope, small size endoscopes, "Basket" for lithotrepsie or stone reducers, "Pig Tail" catheters, future circular anastomotic instruments, small atheroma incisors, as well as new instruments and angioinvasive endoscopic instruments and staplers to be invented in the future or which are currently available and which will be used in other surgical operations.

The sucker may be used independently or in combination with the multi-instrument. One of the principal uses of the sucker in the easy and injury-free handling of adjacent viscera in the patient's body as well as the support and tilting or turning of the organ operated on. It may be also used for haemostatic purposes through the introduction of gauge, small pieces of cotton, other haemostatic material ("Surgi-Cell", "Spongostan"), as well as for diagnostic purposes through the injection of radio opaque substances, the use of ultrasonic heads and miniature cameras 13, designed for exploratory surgery of hollow organs. Furthermore, taking advantage of the sucker bell's negative pressure foreign particles, such as stones, are removed and biopsies are performed.

What is claimed is:

1. Apparatus for laparoscopic-endoscopic surgery arranged to accommodate a plurality of different surgical instruments and to penetrate the abdominal wall through a single hole, the apparatus including a piercing laparoscopic cylinder (1), equipped at its external orifice with a multi-instrument base (11, 12, 13) provided with a plurality of holes (14, 15) for receiving said surgical instruments, characterized in that the piercing laparoscopic cylinder is transversely extendible, the multi-instrument base (12, 12, 13) is elongate and comprises longitudinal ducts registering with said holes (14, 15) and in that the apparatus further comprises a reducer (2) capable of introduction into the piercing laparoscopic cylinder and a number of dividers (3) of variable form and size adapted to be detachably introduced and fitted into the reducer.

2. Apparatus according to claim 1 including a laparoscopic instrument which terminates at a sucker (9) having a concave surface made of elastic or thin metallic foil, said surface having either a predetermined fixed shape or acquiring a readily adjustable shape and size by feeding positive gas pressure into the sucker gas chamber according to existing requirements, the sucker being designed to grasp viscera being operated on.

3. Apparatus according to claim 2, wherein a main instrument body or part of it (6) consists of a system of extensible scissor-like mechanical arms (20), the stems of which have unequal length and are interlinked together and wherein the flexion of such arms is determined by the tension of a wire (6) which runs inside the instrument shaft and is regulated by a spool located on the handle and a pin that achieves the desired flexion for the manipulation thereof.

4. Apparatus according to claim 3 comprising laparoscopic, endoscopic or surgical instruments which are telescopically extendable and thus able to act at variable operating surgery depths.

5. Apparatus according to claim 4 comprising laparoscopic, endoscopic or surgical instruments which can be connected with each other in pairs via mechanical fasteners so as to achieve a controlled single-hand surgical operation.

6. Apparatus according to claim 3 comprising laparoscopic, endoscopic or surgical instruments which can be connected with each other in pairs via mechanical fasteners so as to achieve a controlled single-hand surgical operation.

7. Apparatus according to claim 2 comprising laparoscopic, endoscopic or surgical instruments which are telescopically extendable and thus able to act at variable operating surgery depths.

8. Apparatus according to claim 7 comprising laparoscopic, endoscopic or surgical instruments which can be connected with each other in pairs via mechanical fasteners so as to achieve a controlled single-hand surgical operation.

9. Apparatus according to claim 2 comprising laparoscopic, endoscopic or surgical instruments which can be connected with each other in pairs via mechanical fasteners so as to achieve a controlled single-hand surgical operation.

10. Apparatus according to claim 1 wherein a main instrument body or part of it (6) consists of a system of extensible scissor-like mechanical arms (20), the stems of which have unequal length and are interlinked together and wherein the flexion of such arms is determined by the tension of a wire (6) which runs inside the instrument shaft and is regulated by a spool located on the handle and a pin that achieves the desired flexion for the manipulation thereof.

11. Apparatus according to claim 10 comprising laparoscopic, endoscopic or surgical instruments which are telescopically extendable and thus able to act at variable operating surgery depths.

12. Apparatus according to claim 11 comprising laparoscopic, endoscopic or surgical instruments which can be connected with each other in pairs via mechanical fasteners so as to achieve a controlled single-hand surgical operation.

13. Apparatus according to claim 10 comprising laparoscopic, endoscopic or surgical instruments which can be connected with each other in pairs via mechanical fasteners so as to achieve a controlled single-hand surgical operation.

14. Apparatus according to claim 1 comprising laparoscopic, endoscopic or surgical instruments which are telescopically extendable and thus able to act at variable operating surgery depths.

15. Apparatus according to claim 14 comprising laparoscopic, endoscopic or surgical instruments which can be connected with each other in pairs via mechanical fasteners so as to achieve a controlled single-hand surgical operation.

16. Apparatus according to claim 1 comprising laparoscopic, endoscopic or surgical instruments which can be connected with each other in pairs via mechanical fasteners so as to achieve a controlled single-hand surgical operation.

* * * * *